United States Patent [19]
Vives et al.

[11] Patent Number: 4,711,234
[45] Date of Patent: Dec. 8, 1987

[54] BIO-COMPATIBLE RETENTION PIN, AND A PROSTHESIS INCLUDING SUCH A PIN

[75] Inventors: Michel Vives, Eynes; Bernard Buttazzoni, Marseilles, both of France

[73] Assignee: Societe Europeen de Propulsion, Suresnes, France

[21] Appl. No.: 14,375

[22] Filed: Feb. 10, 1987

[30] Foreign Application Priority Data

Feb. 11, 1986 [FR] France ................. 86 01840

[51] Int. Cl.⁴ .................. A61F 5/04; A61F 2/28; F16B 15/00
[52] U.S. Cl. .................. 128/92 YF; 128/92 YP; 411/446; 411/451; 411/469; 411/922; 411/923; 623/16
[58] Field of Search ........ 128/92 YF, 92 YP, 92 YW, 128/92 YT, 92 YE, 92 YC; 623/16, 18, 23; 411/442, 446–448, 451, 469, 474, 922, 923

[56] References Cited

U.S. PATENT DOCUMENTS

| | | | |
|---|---|---|---|
| 621,737 | 3/1899 | Baker | 411/922 X |
| 1,456,682 | 5/1923 | Steffee | 411/922 X |
| 2,222,338 | 11/1940 | Roberts | 411/446 |
| 3,216,414 | 11/1965 | Street | 411/446 X |
| 3,670,724 | 6/1972 | Bosacco | 623/23 X |
| 3,782,373 | 1/1974 | Smythe | 623/23 X |
| 4,013,071 | 3/1977 | Rosenberg | 623/16 X |
| 4,414,967 | 11/1983 | Shapiro | 128/92 YF X |
| 4,590,928 | 5/1986 | Hunt et al. | 623/16 X |

FOREIGN PATENT DOCUMENTS

0040300 3/1981 European Pat. Off. .
2084468 4/1982 United Kingdom .

*Primary Examiner*—Ronald L. Frinks
*Attorney, Agent, or Firm*—Lowe, Price, LeBlanc, Becker & Shur

[57] ABSTRACT

The invention relates to a retention pin for fixing a support plate or other prosthesis on bone tissue. The pin is made of a material which is bio-compatible with human tissue and comprises two half-pins each having a half-head for bearing against the prosthesis and a retention shank projecting therefrom, with the outline of each shank being semi-cylindrical and with the two half-pins being generally symmetrical to each other about a radial separation plane passing at least partially along the axis of the pin and extending at least as far as the inside faces of the half-heads from which the respective retention shanks project. Said shanks being of sufficient length to project beyond a wall of bone by a distance which is not less than the diameter of the fixing hole through the bone, thereby enabling locking means in the vicinity of the free end of the pin to urge the two half-pins apart from each other so as to urge them resiliently over at least a portion of their length against the inside wall of the fixing hole.

6 Claims, 11 Drawing Figures

BIO-COMPATIBLE RETENTION PIN, AND A PROSTHESIS INCLUDING SUCH A PIN

The present invention relates to a bio-compatible retention pin suitable for fixing a support plate or other prosthesis to bone tissue such as the cortical wall of a bone.

BACKGROUND OF THE INVENTION

In bone surgery, the problem of prosthesis bio-compatibility has only been partially solved heretofore, since although new prostheses and plates in carbon-carbon type composite materials are themselves bio-compatible, such prostheses and plates are currently fixed in place by means of special screws made of titanium or of chromium-cobalt-molybdenum alloy with the threads of the screws engaging in the portion of bone that surrounds fixing holes drilled for this purpose into the bone wall.

It might be supposed that metal screws could be replaced by composite screws of the carbon-carbon type in order to make the entire assembly of support and fixing elements bio-compatible, thereby completely eliminating the risk of prosthesis rejection due to metal alloys.

However, the present design of such special long screws includes a highly tapering thread of small root diameter, which makes it impossible to use composite materials for screws of identical or similar size. The small cross-section of such screws could not withstand the torque applied thereto while the screws were being screwed into place.

One of the aims of the present invention is to provide a bio-compatible retention pin whose structure is suitable for implementation with materials that are less strong than metal alloys.

Naturally the threads of prior art fixing screws penetrate into the bone tissue surrounding the fixing holes either by being screwed into previously tapped holes or else by acting as self-tapping screws, in which case the screw itself cuts its own path through the bone tissue, thereby requiring relatively strong bone tissue in the first place.

Another aim of the invention is to provide a retention pin which avoids any need to make notches or grooves or the like in the wall of pin-receiving fixing holes, and to establish contact with forces extending substantially perpendicularly to the axis and to the cylindrical wall of the fixing holes while still setting up an axial retaining force.

Another aim of the invention is to provide a pin whose cylindrical contact face presses, where appropriate, resiliently against the inside wall of the corresponding fixing hole.

The invention also seeks to provide a retention pin which is locked into place only after one of ends of the pin has passed through the fixing hole and has projected out through the other end thereof.

SUMMARY OF THE INVENTION

The various above aims of the invention are at least partially achieved by providing a retention pin made of a material, such as carbon-carbon, which is bio-compatible with human tissue and which comprises two half-pins each having a half-bearing head and a retention shank rod whose shape is generally semi-cylindrical, with the two half-pins being substantially symmetrical to each other, and with a radial separation plane passing at least partially along the axis of the pin and extending as far as the inner face of the half-head to which the corresponding retention shank is attached, the shank being of sufficient length to project from a bone wall by a distance which is not less than the diameter of the fixing hole, together with locking means in the vicinity of the free end of the pin suitable for moving the two half-pins apart from each other in order to urge them resiliently over at least a portion of their length against the inside wall of the fixing hole.

By virtue of this design, fully bio-compatible prostheses may be provided which are held in place sufficiently strongly, which are easy to put into place, and which are adapted to the mechanical characteristics of composite materials such as carbon-carbon.

BRIEF DESCRIPTION OF THE DRAWINGS

Embodiments of the invention are described by way of example with reference to the accompanying drawings, in which:

FIG. 7 is a cross-section on a line VII—VII of FIG. 3 through an assembly constituted by two opposite portions of the wall of a tubular bone, a support plate pressed against the outside face of said bone, and a second embodiment of the retention pin in accordance with the invention;

MORE DETAILED DESCRIPTION

Figure 1:
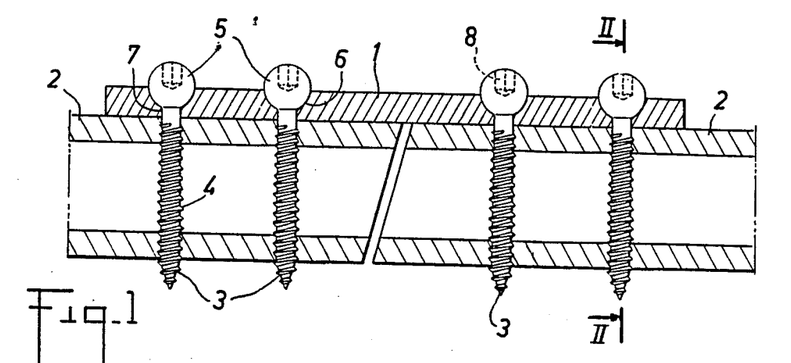
FIGS. 1 and 2 are respectively a longitudinal section and a cross-section through a tubular bone fitted with a prosthesis which is fixed to the bone by means of conventional threaded screws.
Figure 2:
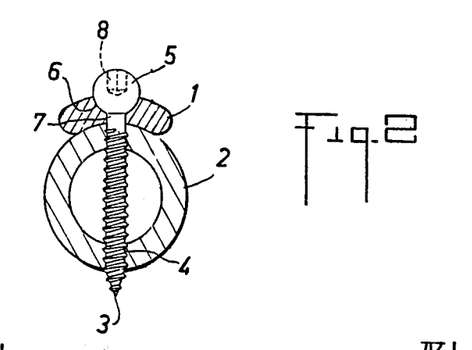
Figure 3:
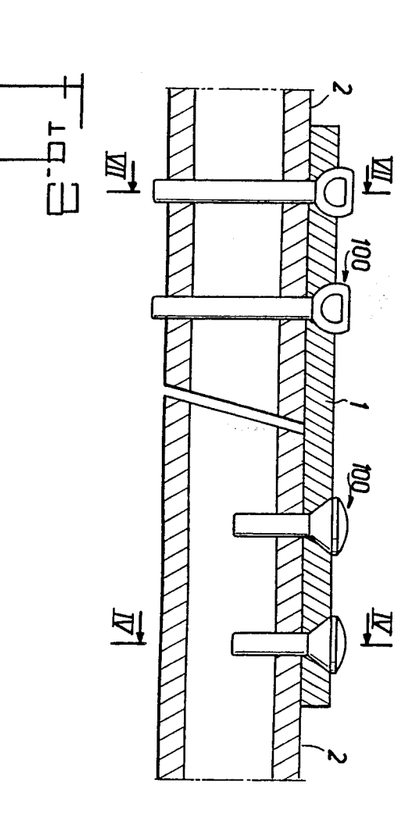
FIG. 3 is a longitudinal section through a tubular bone fitted with a plate or prosthesis which is fixed to the bone by means of a first embodiment (right-hand side of the figure) and by means of a second embodiment (left-hand side of the figure) of a retention pin in accordance with the present invention.

As can be seen in FIGS. 1 and 2, a prosthesis plate 1, e.g. made of carbon-carbon and shaped to match a tubular bone 2, is fixed thereto by means of a plurality of metal screws 3 whose threads 4 each engage in the walls of pairs of aligned fixing holes previously drilled through the tubular bone 2. The screw head 5 generally has a spherical or frusto-conical swelling with the lower portion of the swelling being received in corresponding spherical or frusto-conical recesses counter-sunk in the plate 1, with each of said countersunk recesses extending a hole 7. The top portions of the screw heads 5 generally include a hexagonal recess 8 suitable for receiving an allen key or the like for rotating the screws 3.

The retention pin 10 as shown in FIGS. 3 to 10 of the drawings is made of a bio-compatible material like that of the prosthesis plate 1, for example it may be made of carbon-carbon.

In a first embodiment of the invention, the retention pin 10 comprises two half-pins 11 and 12 each having a half thrust head 13 or 14 at one of its ends and a retention shank 15 or 16 connected to said head 13 or 14. In the embodiment shown in FIGS. 4 to 6, each half thrust head 13, 14 has a hemispherical cap 17, 18 facing away from the shank 15, 16, a semi-cylindrical intermediate length 19, 20, and a semi-frusto-conical portion 21, 22 tapering towards the retention shank 15, 16 whose cross-section coincides with the small base of said frustoconical portion 21, 22, where they meet.

Figure 4:
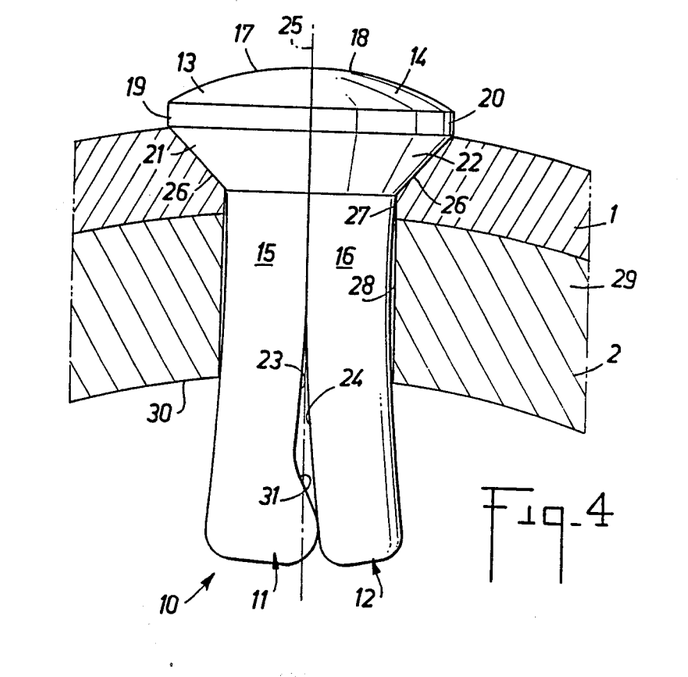
FIG. 4 is a cross-section on line IV—IV of FIG. 3 through an assembly constituted by the cortical wall of a tubular bone, a support plate pressed against the outside face of said bone, and the first embodiment of a retention pin in accordance with the invention.
Figures 5A, 5B:
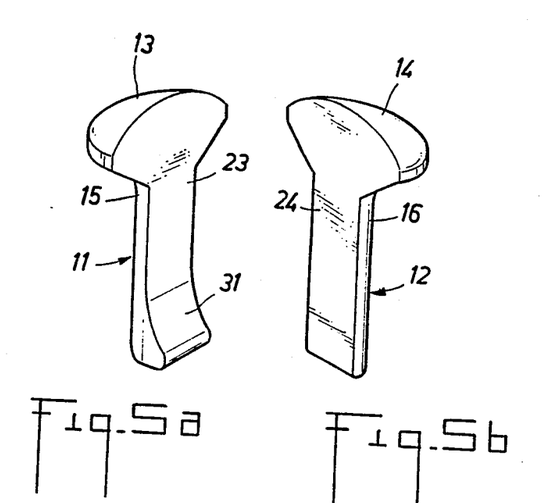
FIGS. 5a and 5b are perspective views of the two halfpins constituting the first embodiment of a retention pin in accordance with the invention.

Each half-pin 11, 12 has a vertical plane contact face 23, 24 extending in a radial plane 25 passing through the axis of the pin 10 when the two half-pins are pressed against each other along their corresponding contact faces 23, 24. The semi-frustoconical portion 21, 22 of each half-pin 11, 12 is received in a corresponding frustoconical recess 26 countersunk in the plate 1; said recess 26 extending a cylindrical hole 27 which is in alignment with a fixing hole 28 drilled in the cortical wall 29 of a tubular bone 2. The fixing hole 28 has an inside diameter which is equal to the inside diameter of the hole 27 and which is slightly greater than the outside diameter of the two half-pins 11 and 12 when assembled and where they pass through the hole 27 in the prosthesis plate 1.

The two half-pins 11 and 12 have retention shanks 15 and 16 of substantially equal length, which length is chosen to be such that the free end of the pin extends beyond the inside face 30 of the cortical wall 29 by a distance which is not less than the diameter of the fixing hole 28.

In the first embodiment shown in FIGS. 3 to 6, the first half-pin 11 (see FIGS. 4 and 5a) includes a locking slope 31 close to its free end, which slope extends from the vertical contact face 23 at a fairly small angle relative to the vertical, e.g. 10° to 15° in a downward direction and towards the vertical contact face 24 of the other half-pin 12 (see FIGS. 4 and 5b). It should be observed that the vertical plane contact face 24 of the second half-pin extends from its "top" (i.e. its head 14 end) right down to its "bottom" or free end. The locking slope 31 co-operates with the bottom portion of the contact face 24 of the second half-pin 12, thereby constituting means for locking the pin 10, and preferably begins at a certain distance from the cortical wall 29, e.g. at a distance equal to about 1 to 1.5 times the radius of the semi-cylindrical periphery of the retention shank 15.

The prosthesis plate 1 is fastened to the tubular bone 2 as follows:

Before placing the plate 1 on the bone 2, a drilling jig is used to drill fixing holes 28 into the cortical wall 29 of said bone, said holes being in alignment with the holes 27 through said plate 1 and having the same diameter. It is recalled that the two semi-cylindrical retention shanks 15 and 16 are symmetrical (apart from the locking slope 31) and have the same diameter as the fixing hole 28 or a slightly smaller diameter than said hole.

The first half-pin 11 having the locking slope 31 is put into place first so that the frusto-conical portion 21 of its half-head 13 is received in the corresponding recess 26. Then, the second half-pin 12 is inserted with its contact face 24 sliding initially along the contact face 23 of the first half-pin 11 until its end meets the locking slope 31. By forcing the second half-pin 12 to continue to advance until its own half-head 14 is also received in the recess 26 in the plate 1, e.g. by means of a hammer or other suitable tool, the free ends of the two half-pins 11 and 12 which extend beyond the fixing hole are caused to splay progressively apart by resilient bending, thereby pressing against the wall of the fixing hole. Since the clamping force is directed perpendicularly to the general axis of the pin 10, it does not generally affect the mechanical strength of the bone because the two half-pins bend at a locking point which is located outside the cortical wall. However, the friction force in the axial direction and above all the wedging effect acting between the fixing hole through the cortical wall 29 and the expanded free end of the pin 10 prevent any axial displacement of one of the half-pins relative to the other and relative to the fixing hole, thus providing good retention of the prosthesis plate 1 on the bone 2, and there is no way of removing the pin 10 without destroying it.

It may be observed that the resilient bending obtained using half-pins in accordance with the invention is much greater than that which would be applicable to metal half-pins. Metal half-pins would rapidly reach the plastic deformation threshold, and as a result the force that they would apply against the wall of the fixing hole would drop off rapidly as a function of the minute displacements to which the half-pins would be subjected in the course of time.

In contrast, by using carbon-carbon material having a much greater resilient bending capability, also termed "spring effect", the forces applied against the wall of the hole persist over time in spite of such minute displacements of the half-pins.

Further, since the resilient bending is large, relatively accurate adjustments can be obtained of the application forces by suitably selecting the dimensions of the parts involved, in particular by suitably selecting the diameter of the fixing hole.

Figure 6:
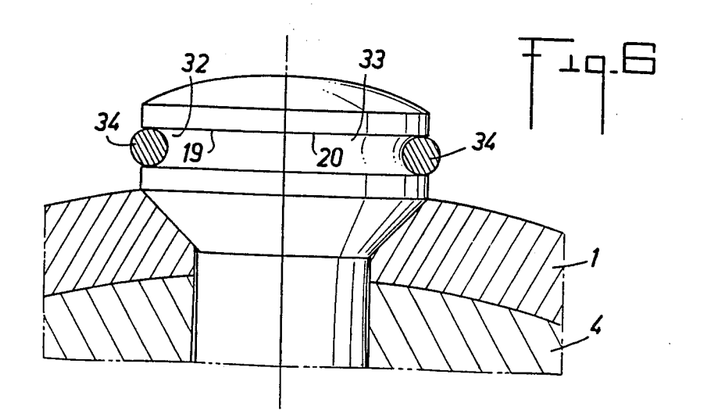
FIG. 6 is a cross-section through a detail of the head portion of a retention pin.
Figure 8:
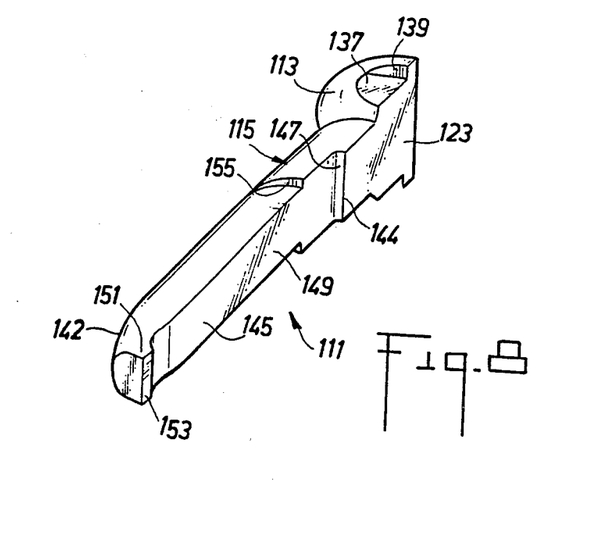
FIG. 8 is a perspective view of a half-pin for use in the second embodiment of the invention.
Figure 9:
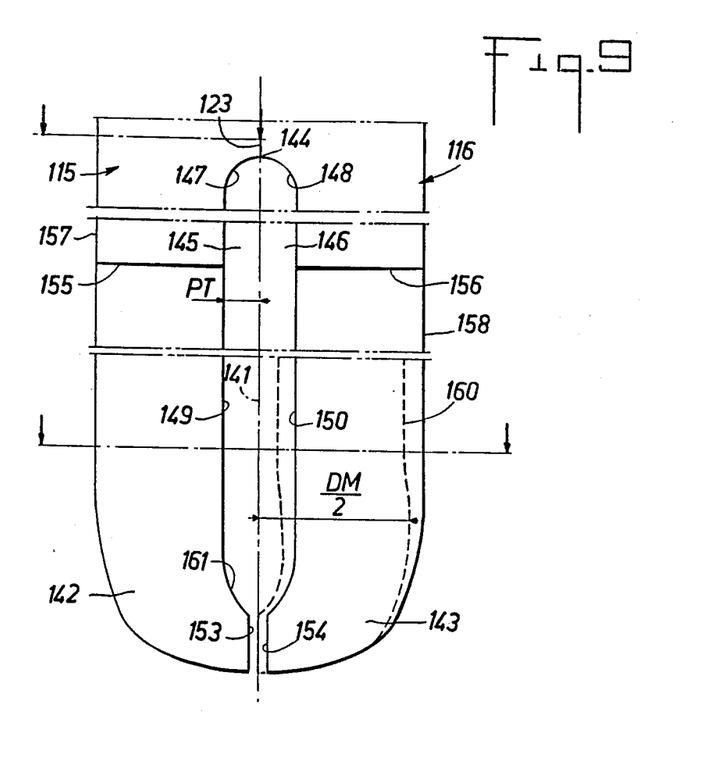
FIG. 9 is an elevation view looking through the mid and the end portions of the second embodiment of a retention pin.
Figure 10:
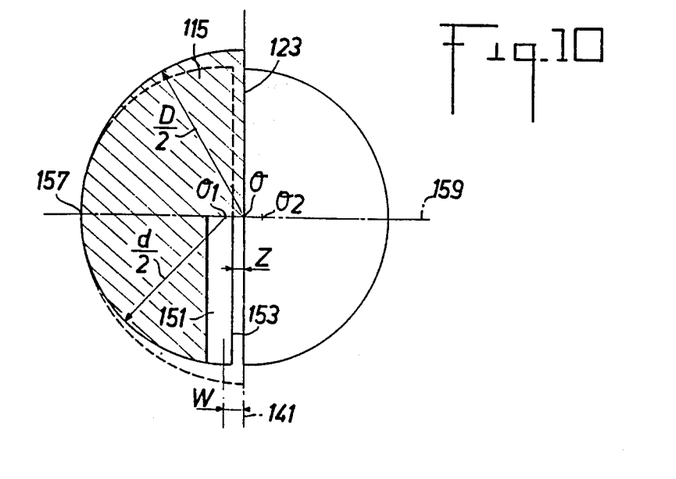
FIG. 10 is a plan view in several horizontal sections which are axially separated from one another of the FIG. 9 retention pin, and of the fixing hole in the bone receiving the end portion of said pin.

In order to prevent a half-pin 11 or 12 from working loose under mechanical or vibrational effects, other means may be provided to cause one half-pin to adhere to the other. For example, the contact face 22 or 23 may be coated at the head end with a bio-compatible glue, or else the semi-cylindrical portion 19, 20 of the head may be provided with an annular groove 32, 33 and a split ring 34 may be lodged therein, which ring may likewise be made of bio-compatible material such as carbon-carbon.

The retention of the pin 10 is rapidly consolidated by bone tissue colonization around the free end of the pin 10 and in the gap formed between the separated portions of the contact faces 23 and 24 of the half-pins 11 and 12.

It has been observed experimentally that this bone tissue colonization provides two different kinds of advantage:

firstly, the colonization in the gap between the two half-pins considerably reduces the risk of relative axial sliding between the two half-pins; and secondly, the colonization around the free ends projecting through the fixing hole constitutes a block which surrounds said free ends and supports them so that it becomes practically impossible to remove the pin from the hole.

The retention pin 110 shown in FIGS. 7 to 10 corresponds to a second embodiment of the invention and is intended more particularly, but not exclusively, for use when the pin is to pass through two opposite portions of the cortical wall of a single tubular bone. In this second embodiment, the retention pin 110 is likewise constituted by two half-pins 111 and 112 having corresponding bearing half-heads 113 and 114 which in this case are nearly entirely hemispherical in shape with a horizontal plane top bearing face 135, 136 perpendicular to the axis of the pin 110 and with two opposite vertical parallel plane faces 137 and 138 having outwardly-directed shoulders 139 and 140 running along the tops thereof. In this particular case, the half-pins 111 and 112 are completely symmetrical about a plane of symmetry 141 containing the axis of the pin. Each half-pin 111 and 112 has a retention shank 115 or 116 extending below the corresponding half-head 113 or 114, with the outer surfaces of the shanks being generally semi-cylindrical and tapering slightly towards their free ends in order to terminate in respective semi-frustoconical portions 142 and 143.

The top portion of each half-pin 111 and 112 has a contact face 123, 124 which lies in the plane of symmetry 141 when the two half-pins 111 and 112 are assembled to constitute a single pin 110. These two contact faces 123 and 124, each of which occupies a radial plane of a corresponding half-pin 111 or 112, extends only over a portion of the total length of the pin 110, and preferably over a portion which is longer than the thickness of the prosthesis plate 101 plus the adjacent cortical wall 129, but which is shorter than the sum of the thickness of the plate 101 and the corresponding radius of the tubular bone 102.

Generally speaking, the length of the contact faces 123 and 124 is such that the common bottom edges 144 thereof project beyond the inside face 130 of the cortical wall 129 adjacent to the plate 101 by a distance of about the radius of the semi-cylindrical outline of the retention shanks 115 and 116.

Beyond said common bottom edges 144, the contact faces 123 and 124 of each half-pin 111 and 112 has a relatively shallow recess 145, 146 with the depth PT of each recess being a few tenths of a millimeter. The top ends of the recesses run from the common bottom edge 144 of the contact faces 123 and 124 in the form of respective curved portions 147 and 148 leading to respective flat bottoms 149 and 150 running parallel to the plane of symmetry 141 and to the contact faces 123 and 124. The bottom ends of the recesses in the vicinity of the free ends 142 and 143 of the retention shanks 115 and 116 are constituted by locking slopes 151 and 152 extending parallel to the common bottom edge 144 of the contact faces 123 and 124 and running up to bearing faces 153 and 154 which extend parallel to the top contact faces 123 and 124 and to the plane bottoms 149 and 150 of the recesses 145 and 146.

As can be seen in FIG. 7, the length of the pin 110, and in particular of its retention shanks 115 and 116 is sufficient for the free ends 142 and 143 of the shanks 115 and 116 to project out through the other side of the bone opposite from the side of the bone which is in contact with the plate 101, after the pin 110 has been put into place through the plate 101 and the tubular bone 102. The free ends project by a distance which is about the same as the diameter of the pin 110 when the shanks are assembled.

The outer periphery of each retention shank 115 and 116 is sub-divided into two portions by a horizontal shoulder 155 or 156 which tapers progressively from the flat bottom 149 or 150 of the corresponding recess out to the generator line 157 or 158 situated in the radial plane passing through the axis of the pin 110 and extending perpendicularly to the plane of symmetry 141 of the contact faces 123 and 124, of the recess bottoms 149 and 150, and of the recesses 145 and 146. These horizontal shoulders 155 and 156 are located about one-third of the way along the recesses 145 and 146 from their head ends.

The top portion of each retention shank 115 and 116 situated above the horizontal mid-shoulder 155 or 156 has a semi-cylindrical outline whose cross-section is a semi-circle of diameter D having its origin O on the general axis and in the plane of symmetry 141 of the retention pin 110, with the cross-section of the pin 110 as a whole at this level being a circle of diameter D.

The bottom portion of each retention shank 115 and 116 beneath the mid-shoulder 155 or 156 also comprises a semi-cylindrical outline whose axis lies in a radial plane 159 perpendicular to the plane of symmetry 141 of the pin 110 and passing through the general axis thereof, such that the cross-section of the bottom portion of each retention shank is also in the form of a semi-circle of diameter d which is less than the diameter D, and which has its origin 01 or 02 situated in the radial plane 159 on either side of the plane of symmetry 141 and at a distance W from the plane of symmetry.

In this second embodiment, the prosthesis plate 101 includes a hemispherical recess 126 countersunk to receive the bottom portions of the half-heads 113 and 114 of the half-pins 111 and 112, said recess running into a cylindrical hole 127 through which the retention shanks 115 and 116 pass. The diameter of the hole 127 is slightly greater than diameter D of the first hole 128 drilled through the portion of the cortical wall which is adjacent to the prosthesis plate 101, with said diameter D being the same as the diameter of the cylindrical outline of the top portion of the pin 110. Opposite to the first hole 128 through the bone, the cortical wall 129 of the tubular bone 102 is provided with a second through hole 160 which is coaxial with the first hole 128 and which has a diameter d equal to the outside diameter d of the cylindrical outline of the bottom portions of the retention shanks 115 and 116.

The lateral offset W of the centers 01 and 02 of the semicircles of the cross-sections of the bottom portions of the retention shafts 115 and 116 is determined by the equation:

$$W=(D-d)/2$$

where D is the diameter of the first hole 128 and of the semi-circles of the cross-sections of the top portions of the semi-cylindrical retention shanks 115 and 116, and d is the diameter of the semi-circular cross-sections of the bottom portions of the retention shanks 115 and 116 and also the diameter of the second hole 160.

By way of specific example, D may be 4.5 mm, while d may be 4.0 mm.

The consequence of this particular arrangement is that only those generator lines 157 and 158 lying in the radial plane 159 which extends perpendicular to the plane of symmetry 141 are constituted by uninterrupted straight lines which are common both to the top portions and to the bottom portions of the retention shanks 115 and 116, whereas all the other generator lines of the semi-cylindrical outlines of these shanks 115 and 116 are interrupted at the transverse shoulders 155 and 156.

As mentioned above, the bottom portions of the recesses 145 and 146 are delimited by locking slopes 151 and 152 which run smoothly from the bottoms 149 and 150 of said recesses 145 and 146 and lead to vertical bearing faces 153 and 154 which are located at a distance Z from the plane of symmetry 141 when the two half-pins 111 and 112 are assembled without stresses being applied thereto while their contact faces 123 and 124 rest against each other. The value of Z is preferably about 3W/5 and the value of PT is about 2W.

Under these circumstances, the two bearing faces 153 and 154 at the ends of the locking slopes 151 and 152 are separated from each other by a gap equal to 2Z or 6W/5 when the two contact faces 123 and 124 are resting against each other and no other stress is applied to the two assembled half-pins 111 and 112.

In this case, the two generator lines 157 and 158 are separated from each other, even in the bottom portion of the pin, by a distance equal to D.

When a prosthesis plate 101 is being fixed to the bone 102, and after the two coaxial fixing holes 128 and 160 of different diameters D and d have been drilled, the first half-pin 111 is passed through the hole 127 and the two fixing holes 128 and 160. In this case, the bottom portion of the first half-pin 111 is deflected towards the plane of symmetry 141 since the wall of the second fixing hole is radially offset towards the general axis of the pin 110 by an amount (D−d)/2 relative to the first fixing hole 128, and as a result the generator line 157 is initially placed at a slight angle relative to the vertical so that the retention shank 115 can pass through the second fixing hole 160. When the first half-head 113 comes to rest in the recess 126 in the prosthesis plate 101, the second half-pin 112 is inserted and passes easily since its bottom end 143 can slide freely without encountering any obstacles along the recess 145 of the first half-pin 111 until it reaches the curved portion 161 of the locking slope 151 of the first half-pin 111.

The resulting camming action on the bottom end 143 of the second half-pin 112 as it moves downwardly along the slope 161 urges both end portions 142 and 143 away from each other and resiliently away from the plane of symmetry 141 until the bearing faces 154 and 153 come into contact and are strongly urged against each other by elastic forces. When this happens, both retention shanks 115 and 116 bend slightly and resiliently, moving towards each other into their respective recesses 145 and 146 within the second fixing hole 160, while simultaneously bending away from each other up to their ends, thereby forming wedges beyond said second hole 160.

The diameter d of the second fixing hole is less than the distance D between the two generator lines 157 and 158, and is also less than the maximum dimension DM of the cross-section of the bottom end of the pin 110 where it projects beyond the second hole 160, with said maximum dimension DM taken in the radial plane 159 being given by the following equation:

$$DM = 2(d/2 + W - Z)$$

whence $$DM = d + 4W/5 \text{ for } Z = 3W/5$$

Using the following numerical values: D=4.5 mm; d=4.00 mm; W=0.25 mm; and Z=0.15 mm; then DM=4.2 mm. In other words, the wedging effect applied by the two retention shanks 115 and 116 to the bottom wall of the second fixing hole 160 is due to the cylindrical faces of the bottom ends of the two shanks 115 and 116 moving apart by 0.2 mm. It will also be observed that in the second fixing hole 160, the bottoms 149 and 150 of the recesses 145 and 146 are resiliently inwardly deflected by a value equal to W in order to allow the cylindrical outlines of the shanks 115 and 116 to match the diameter d of the second hole 160.

As mentioned above, the retaining effect of the pin 110 is rapidly consolidated by a colonization of bone tissue around the pin 110 on either side of the cortical wall 102 and in the space formed by the two recesses 145 and 146 in the two half-pins 111 and 112.

Since the contact or locking point of the pin 110 (i.e. the locking slopes 151 and 152) lies outside the cortical wall 102 and is therefore accessible from the outside, the pin 110 is easier to disassemble, should that become necessary, than is the case with conventional systems.

Naturally, other variants of the invention may be implemented using a mutual wedging and locking effect of two half-pins without going beyond the scope of the present invention as defined by the accompanying claims.

The invention also extends to bio-compatible prosthesis plates suitable for being fixed to bones using a bio-compatible pin in accordance with the invention.

We claim:

1. A retention pin for fixing a support plate or other prosthesis onto bone tissue, e.g. onto the cortical wall of a bone, said pin being made of a material which is bio-compatible with human tissue and comprising two half-pins each having a respective half-head for bearing against the plate, and a retention shank of generally semi-cylindrical outline, said half-pins being generally symmetrical to each other about a radial separation plane passing at least in part along the pin axis and extending up to the inside face of each half-head from which the respective retention shanks project, each shank being sufficiently long to pass through a wall of bone and to project therebeyond by a distance which is not less than the diameter of the fixing hole through said wall of bone, each shank also including locking means in the vicinity of the free end of the pin suitable for urging the two half-pins apart from each other so as to press them resiliently over at least a portion of their length against the inside wall of the fixing hole.

2. A retention pin according to claim 1, wherein each half-pin includes a plane contact face, at least in the vicinity of its head end, said contact face being suitable for resting against the other half-pin.

3. A retention pin according to claim 2, wherein the first half-pin includes a locking slope in the vicinity of its free end, said locking slope extending downwardly from the vertical contact face of said first pin at a fairly small angle towards the contact face of the other half-pin, in order to co-operate therewith so as to mutually separate the bottom ends of the two half-pins when engaged in a fixing hole through a wall of bone, and in order to produce a wedging effect relative to the wall of said fixing hole.

4. A retention pin according to claim 2, wherein the two halfpins are sufficiently long to pass through coaxial holes of different diameters made through a tubular bone so that their free ends project therebeyond by a distance equal to about the diameter of the assembled pin, wherein the contact faces extend from the top or head portion of the half-pins over a distance greater than the thickness of the prosthesis plate and of the adjacent cortical wall of the tubular bone, wherein each half-pin includes a shallow recess extending from beyond the common bottom edges of the contact faces in the form of a slope connecting said bottom edges to respective plane recess bottoms running parallel to the contact faces of the half-pins and to the plane of symmetry of the assembled pin, said recesses terminating at the free ends of each retention shank in the form of a locking slope including a bearing face for engaging the bearing face of the other retention shank and serving to urge the free ends of the locking shanks away from each other, and wherein the outline of each retention shank is sub-divided into two semi-cylindrical portions by a horizontal shoulder which tapers progressively from the flat bottom of the corresponding recess up to the generator line situated in the radial plane perpendicular to the plane of symmetry.

5. A retention pin according to claim 1, wherein the locking and contact point between the two half-pins is situated outside the cortical wall of the bone.

6. An assembly comprising a prosthesis and bio-compatible pins according to claim 1.

* * * * *